US012788597B2

(12) United States Patent
Logan et al.

(10) Patent No.: US 12,788,597 B2
(45) Date of Patent: Nov. 10, 2026

(54) ENDOPROSTHESIS AND METHODS FOR TREATING NON-THROMBOTIC ILIAC VEIN LESIONS

(71) Applicant: BOSTON SCIENTIFIC SCIMED, INC., Maple Grove, MN (US)

(72) Inventors: Brady Scott Logan, Monticello, MN (US); Paul F. Chouinard, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 551 days.

(21) Appl. No.: 18/238,630

(22) Filed: Aug. 28, 2023

(65) Prior Publication Data

US 2024/0065864 A1 Feb. 29, 2024

Related U.S. Application Data

(60) Provisional application No. 63/402,206, filed on Aug. 30, 2022.

(51) Int. Cl.
*A61F 2/848* (2013.01)
*A61F 2/844* (2013.01)
(Continued)

(52) U.S. Cl.
CPC .............. *A61F 2/848* (2013.01); *A61F 2/844* (2013.01); *A61F 2/86* (2013.01); *A61F 2/06* (2013.01);
(Continued)

(58) Field of Classification Search
CPC ...... A61F 2/04; A61F 2/06; A61F 2/07; A61F 2/2418; A61F 2/82; A61F 2/86;
(Continued)

(56) References Cited

U.S. PATENT DOCUMENTS 9,308,110 B2 * 4/2016 Newell .................. A61F 2/966
2002/0055772 A1 5/2002 McGuckin et al.
(Continued)

OTHER PUBLICATIONS

International Search Report and Written Opinion dated Nov. 30, 2023 for International Application No. PCT/US2023/031238.
Gibson, "Illiac Vein Stenting: Best Practices for Patient Safety and Successful Outcomes," Medtronic Medical Affairs Corner, 42 pages, 2021.

*Primary Examiner* — Dinah Baria
(74) *Attorney, Agent, or Firm* — Seager, Tufte & Wickhem LLP

(57) ABSTRACT

An endoprosthesis for preventing collapse of a vein may include an expandable framework configured to shift between a radially collapsed configuration and a radially expanded configuration, and a plurality of anchoring legs extending axially away from a first end of the expandable framework. The plurality of anchoring legs may be configured to shift between a delivery configuration and a deployed configuration. In the deployed configuration, the plurality of anchoring legs may be configured to extend radially outward of the expandable framework in the radially expanded configuration. A system for preventing collapse of a vein may include a delivery catheter having a lumen, an endoprosthesis disposable within a distal portion of the lumen in a radially collapsed configuration, and at least one filament coupled to the plurality of anchor legs of the endoprosthesis and extending within the lumen of the delivery catheter.

4 Claims, 12 Drawing Sheets

(51) Int. Cl.

| | |
|---|---|
| ***A61F 2/86*** | (2013.01) |
| *A61F 2/06* | (2013.01) |
| *A61F 2/82* | (2013.01) |
| *A61F 2/90* | (2013.01) |

(52) U.S. Cl.
CPC ........... *A61F 2/82* (2013.01); *A61F 2002/825* (2013.01); *A61F 2002/8483* (2013.01); *A61F 2002/8486* (2013.01); *A61F 2/90* (2013.01); *A61F 2220/0016* (2013.01); *A61F 2230/0069* (2013.01); *A61F 2250/0098* (2013.01)

(58) Field of Classification Search
CPC .... A61F 2/90; A61F 2/848; A61F 2002/8483; A61F 2002/8486
See application file for complete search history.

(56) References Cited

U.S. PATENT DOCUMENTS

| | | | | |
|---|---|---|---|---|
| 2010/0082089 | A1 | 4/2010 | Quadri et al. | |
| 2011/0264196 | A1* | 10/2011 | Savage ................. | A61F 2/2418 623/2.11 |
| 2017/0281375 | A1 | 10/2017 | Longo et al. | |
| 2018/0055629 | A1* | 3/2018 | Oba ...................... | A61F 2/2409 |
| 2018/0318115 | A1 | 11/2018 | Chinubhai et al. | |
| 2021/0121130 | A1 | 4/2021 | Nagy et al. | |

* cited by examiner

ENDOPROSTHESIS AND METHODS FOR TREATING NON-THROMBOTIC ILIAC VEIN LESIONS

CROSS REFERENCE TO RELATED APPLICATIONS

This application claims the benefit of priority of U.S. Provisional Application No. 63/402,206 filed Aug. 30, 2022, the entire disclosure of which is hereby incorporated by reference.

TECHNICAL FIELD

The present disclosure pertains to medical devices, and methods for manufacturing and/or using medical devices. More particularly, the present disclosure pertains to an improved design and/or methods for an endoprosthesis or stent for treating non-thrombotic iliac vein lesions.

BACKGROUND

Stents, grafts, stent-grafts, and similar implantable medical devices, collectively referred to hereinafter as stents, are radially expandable or self-expanding endoprostheses which are intravascular or endoscopic implants capable of being implanted transluminally either percutaneously or endoscopically. Stents may be implanted in a variety of body lumens or vessels such as within the vascular system, urinary tracts, bile ducts, gastro-intestinal tract, airways, etc. Stents may be used to open constricted body lumens. Stents may be used to reinforce body vessels and to prevent restenosis following angioplasty in the vascular system. They may be self-expanding, mechanically expandable, or hybrid expandable. In general, self-expanding stents are mounted on a delivery device consisting of two tubes. The stent is delivered by sliding the outer tube to uncover and release the stent.

Stents are typically tubular members that are radially expandable from a reduced diameter configuration for delivery through a patient's body lumen to an expanded configuration once deployed at the treatment site. The stent may be formed from a tubular member in which a pattern is subsequently formed by etching or cutting material from the tubular member, or it may be made from wires or filaments using techniques such as braiding, knitting, or weaving. Stents may often rely on radial outward force to anchor the stent in place within the body lumen. Venous stenting may present different characteristics and/or results than arterial stenting due to anatomical differences. Depending on the specific circumstances of the treatment, certain stent characteristics may work in opposition to each other. There remains an ongoing need for new stent designs and/or configurations that better balance and/or incorporate the various stent characteristics.

SUMMARY

In one example, an endoprosthesis for preventing collapse of a vein may comprise an expandable framework configured to shift between a radially collapsed configuration and a radially expanded configuration, the expandable framework having a first end and a second end opposite the first end, and a plurality of anchoring legs extending axially away from the first end of the expandable framework, the plurality of anchoring legs being configured to shift between a delivery configuration and a deployed configuration. In the deployed configuration, the plurality of anchoring legs may be configured to extend radially outward of the expandable framework in the radially expanded configuration.

In addition or alternatively to any example described herein, the expandable framework is self-biased toward the radially expanded configuration.

In addition or alternatively to any example described herein, the plurality of anchoring legs is self-biased toward the deployed configuration.

In addition or alternatively to any example described herein, the endoprosthesis may further comprise a plurality of anchoring barbs extending radially outward from the plurality of anchoring legs.

In addition or alternatively to any example described herein, the plurality of anchoring legs includes a plurality of paddles configured to engage a wall of the vein.

In addition or alternatively to any example described herein, each paddle of the plurality of paddles is disposed opposite the first end of the expandable framework.

In addition or alternatively to any example described herein, each paddle of the plurality of paddles includes at least one aperture formed therein.

In addition or alternatively to any example described herein, each paddle of the plurality of paddles includes at least one radiopaque marker.

In addition or alternatively to any example described herein, when unconstrained, the plurality of paddles defines a radial extent that is at least 10% greater than a radial extent of the expandable framework.

In addition or alternatively to any example described herein, when unconstrained, the radial extent defined by the plurality of paddles is at least 20% greater than the radial extent of the expandable framework.

In addition or alternatively to any example described herein, a system for preventing collapse of a vein may comprise a delivery catheter having a lumen extending therethrough, an endoprosthesis disposable within a distal portion of the lumen in a radially collapsed configuration, the endoprosthesis including: an expandable framework configured to shift between the radially collapsed configuration and a radially expanded configuration, the expandable framework having a first end and a second end opposite the first end; and a plurality of anchoring legs extending axially away from the first end of the expandable framework, the plurality of anchoring legs being configured to shift between a delivery configuration and a deployed configuration; wherein, in the deployed configuration, the plurality of anchoring legs is configured to extend radially outward of the expandable framework in the radially expanded configuration; and at least one filament coupled to the plurality of anchor legs of the endoprosthesis and extending within the lumen of the delivery catheter.

In addition or alternatively to any example described herein, the plurality of anchoring legs extends proximally from the expandable framework.

In addition or alternatively to any example described herein, the plurality of anchoring legs includes a plurality of paddles configured to engage a wall of the vein, and the at least one filament is releasably coupled to the plurality of paddles.

In addition or alternatively to any example described herein, the system may further comprise a plurality of anchoring barbs extending radially outward from the plurality of anchoring legs. The at least one filament and the delivery catheter may cooperate to change an angle of the plurality of anchoring barbs relative to a central longitudinal axis of the expandable framework.

In addition or alternatively to any example described herein, a method of preventing collapse of a vein may comprise positioning a distal end of a delivery catheter adjacent a treatment site within the vein, the delivery catheter having a lumen extending therethrough; and deploying an endoprosthesis at the treatment site. The endoprosthesis may include an expandable framework configured to shift between the radially collapsed configuration and a radially expanded configuration, the expandable framework having a first end and a second end opposite the first end, and a plurality of anchoring legs extending axially away from the first end of the expandable framework, the plurality of anchoring legs being configured to shift between a delivery configuration and a deployed configuration. In the deployed configuration, the plurality of anchoring legs may be configured to extend radially outward of the expandable framework in the radially expanded configuration. After deploying the endoprosthesis at the treatment site, the plurality of anchoring legs may extend upstream from the expandable framework within the vein.

In addition or alternatively to any example described herein, prior to positioning the distal end of the delivery catheter adjacent the treatment site, the delivery catheter is advanced into the vein at a location upstream of the treatment site.

In addition or alternatively to any example described herein, the expandable framework is sized and configured to prevent external compression of the vein at the treatment site while simultaneously avoiding radial stretching of the vein at the treatment site.

In addition or alternatively to any example described herein, the method may further comprise recapturing the endoprosthesis within the lumen of the delivery catheter and repositioning the endoprosthesis at and/or adjacent to the treatment site.

In addition or alternatively to any example described herein, the expandable framework comprises a plurality of closed cells.

In addition or alternatively to any example described herein, the treatment site is a non-thrombotic iliac vein lesion.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
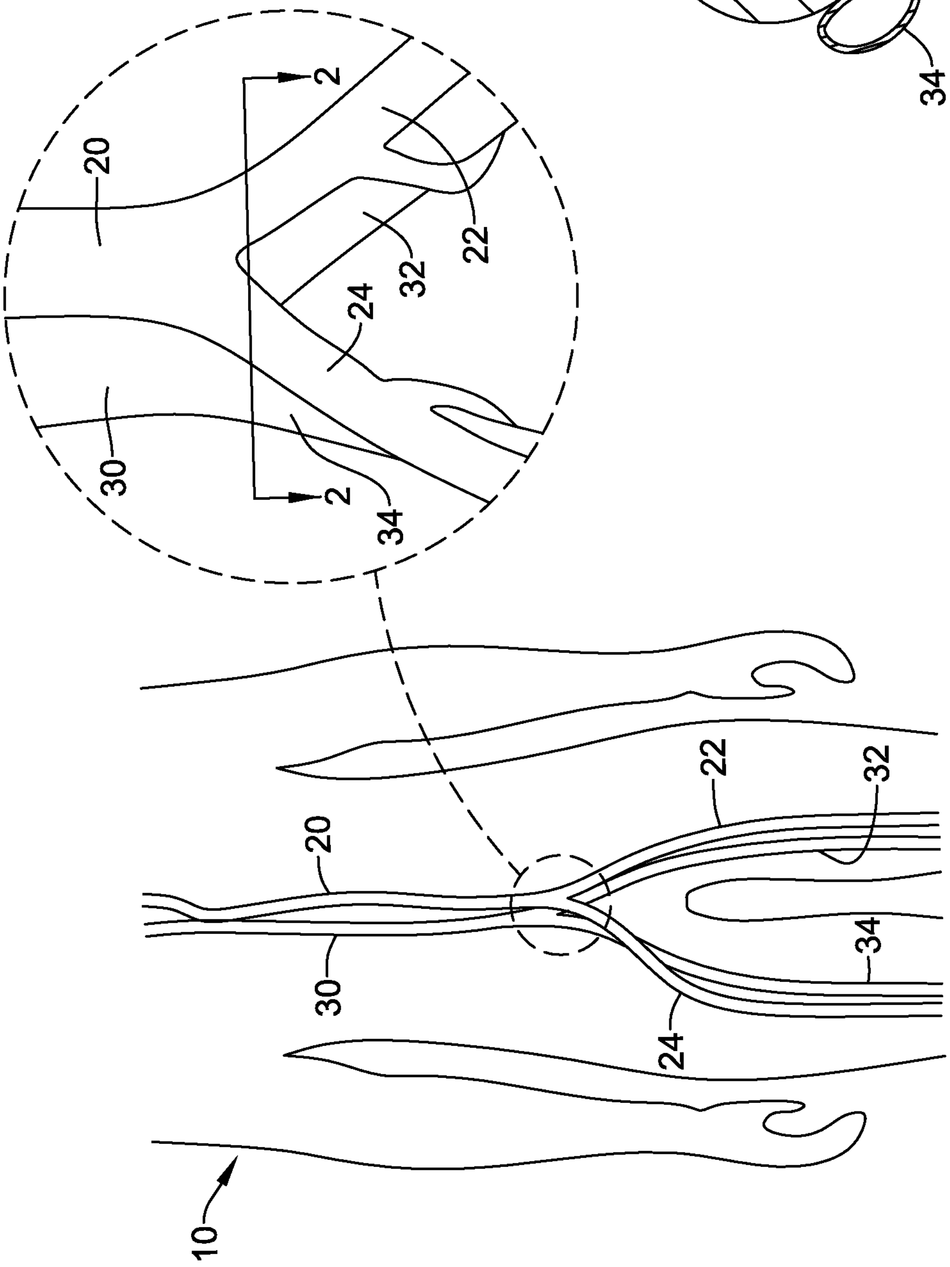
FIG. 1 is a schematic illustration of selected aspects of the anatomy of a patient related to non-thrombotic iliac vein lesions.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the disclosure are not necessarily shown in each figure or discussed in detail below. However, it will be understood that the following discussion may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

Figure 2:
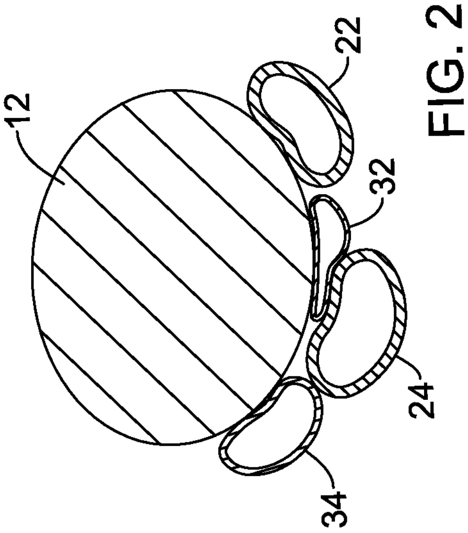
FIG. 2 is cross-sectional view of a selected portion of the anatomy of a patient having a non-thrombotic iliac vein lesion.
Figure 3:
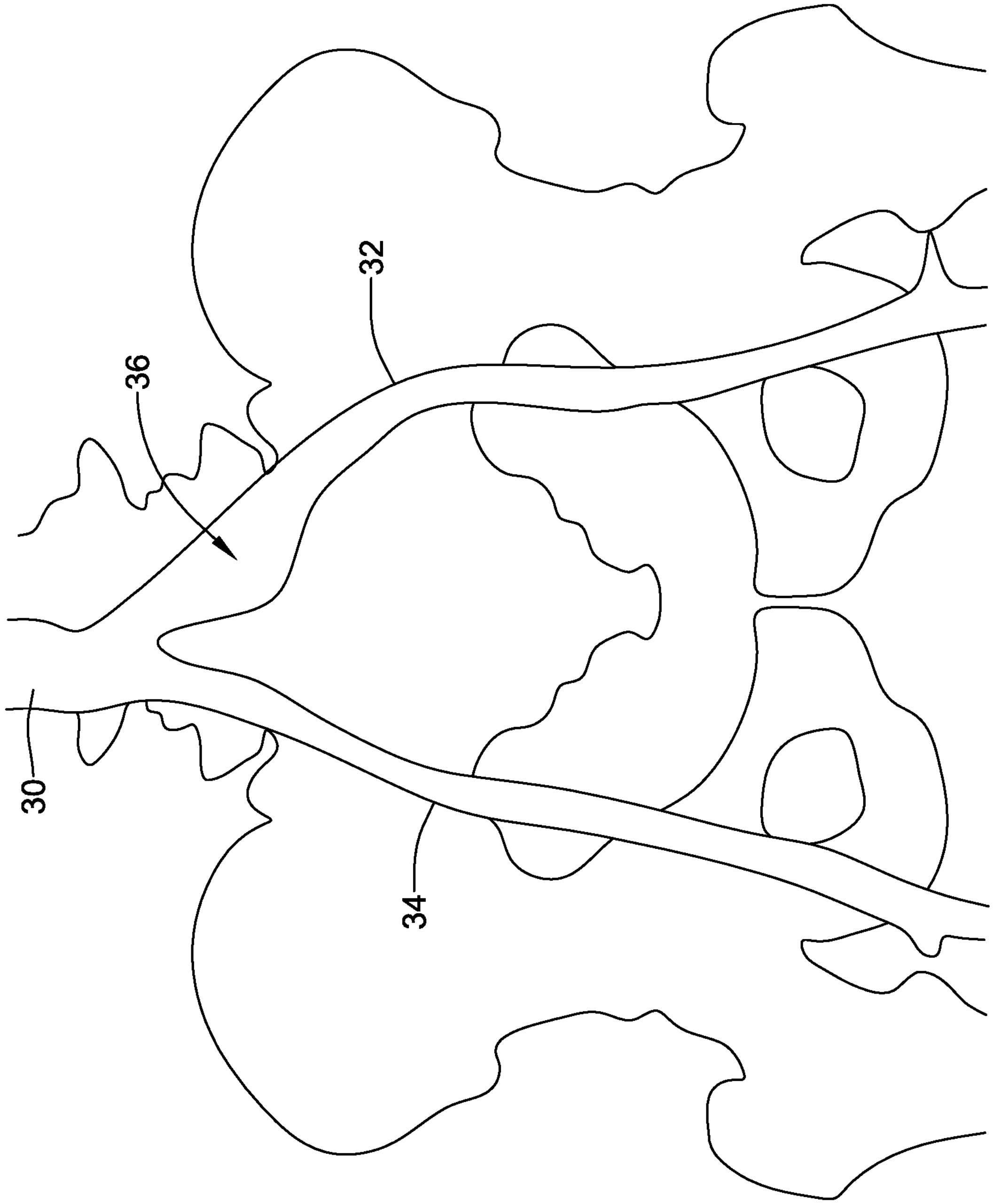
FIG. 3 is a schematic illustration showing a distention that may result from a non-thrombotic iliac vein lesion.

FIG. 1 illustrates the aorta 20 and inferior vena cava 30 of a patient 10. Near the pelvis of the patient 10, the aorta 20 splits into the left common iliac artery 22 and the right common iliac artery 24, and the inferior vena cava 30 splits into the left common iliac vein 32 and the right common iliac vein 34. In some patients, where the right common iliac artery 24 overlaps the left common iliac vein 32, the right common iliac artery 24 may compress the left common iliac vein 32 against the spine 12 of the patient 10, as seen in FIG. 2, thereby causing a non-thrombotic iliac vein lesion adjacent to the junction of the left common iliac vein 32, the right common iliac vein 34, and the inferior vena cava 30. In some cases, a non-thrombotic iliac vein lesion may obstruct blood flow, resulting in elevated venous blood pressure, pain, leg swelling, and/or blood clot formation. Additionally, in some patients, a non-thrombotic iliac vein lesion may cause a distention 36 to form in the left common iliac vein 32 immediately upstream of the non-thrombotic iliac vein lesion, as shown in FIG. 3.

Some accepted treatments of non-thrombotic iliac vein lesions include placement of a stent, commonly formed as a braided stent or a laser cut stent, within the non-thrombotic iliac vein lesion and extending upstream therefrom within the left common iliac vein 32 to anchor the stent in place. Stent placement at this location may be difficult. The braided stents typically used have low resistance to compression at their ends but are flexible and offer several desirable characteristics for stenting a vein. Unfortunately, spanning the opening of the right common iliac vein 34 into the inferior vena cava 30 such that a middle portion of the braided stent offering higher compression resistance and/or high outward radial force is positioned within the non-thrombotic iliac vein lesion may cause problems of its own (e.g., thrombus formation, flow restriction, etc.).

Figure 4:
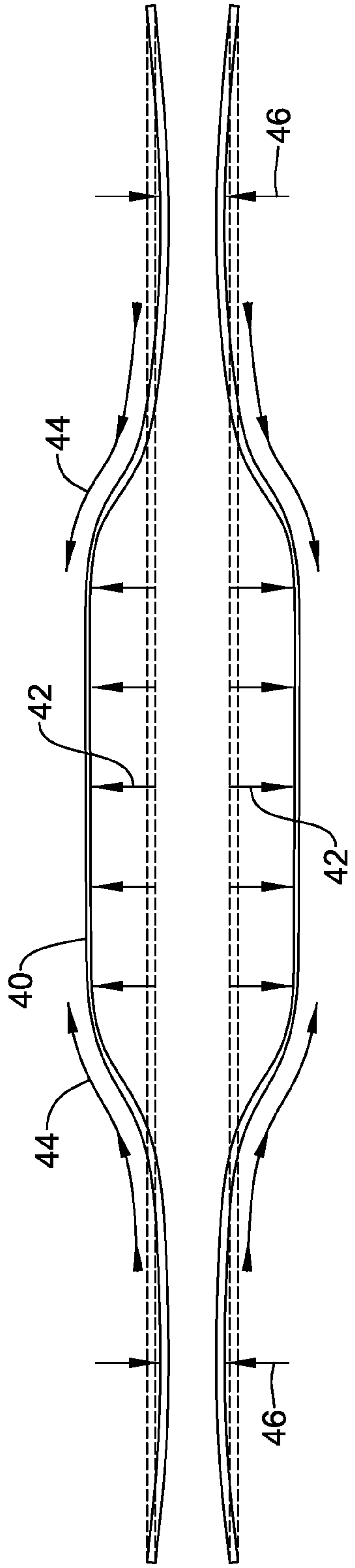
FIG. 4 illustrates the Poisson effect that may result when stenting a vein.

It has been found that expandable stents, which are typically oversized and formed from nitinol or other shape memory material, stretch the vessel in order to both expand the vessel lumen and anchor the expandable stents due to chronic outward force, and may cause pain, discomfort, and/or vessel erosion. Chronic outward force is driven significantly by the amount of oversizing and its value in veins is primarily in anchoring the stent. Oversizing the stent within a vein 40, which tends to stretch more than an artery under the same chronic outward force, may result in the Poisson effect, which redistributes a radially applied force 42 (e.g., the chronic outward force) to the longitudinal direction 44, as seen in FIG. 4. As shown in FIG. 4, immediately upstream and downstream of where the vein 40 is stretched radially outward by the radially applied force 42 (e.g., the chronic outward force), the vein 40 narrows (e.g., at reference 46), which may negatively affect flow characteristics within the vein 40. The Poisson effect is more pronounced in veins than arteries and creates challenges when stenting veins. In order to avoid the Poisson effect in veins, as well as reduce inflammation and pain, some physicians will limit oversizing of the stent and/or may even size the stent in a 1:1 ratio with the vessel (e.g., place a 16 mm stent in a 16 mm vessel) in order to exert the least amount of chronic outward force possible on the vein. However, undersizing the stent increases the risk of stent migration due to reduced anchoring forces.

Figure 5:
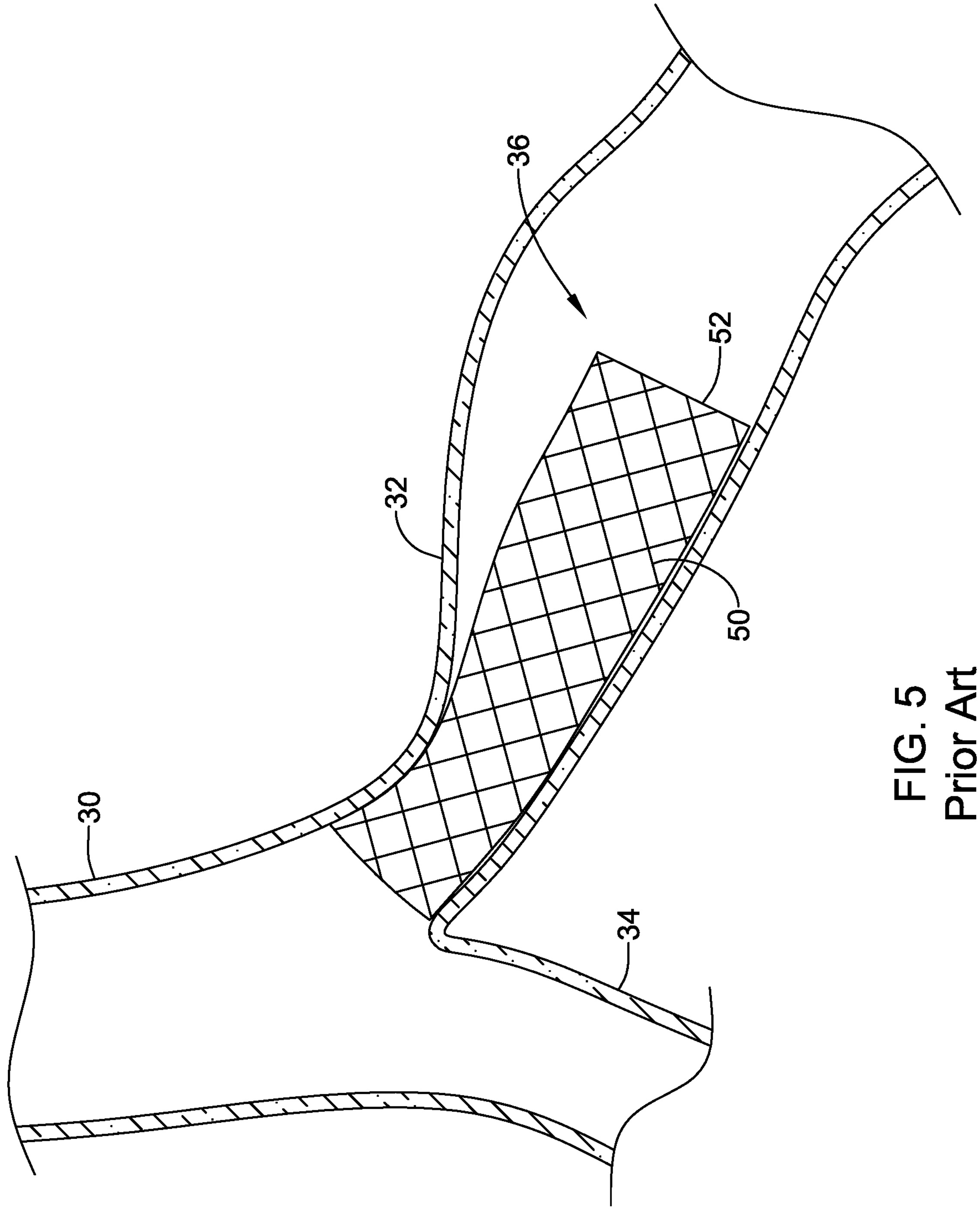
FIG. 5 Prior Art
FIG. 5 schematically illustrates selected characteristics of an accepted treatment for a non-thrombotic iliac vein lesion in a vessel having the distention of FIG. 3.

Referring back briefly to FIG. 3, the non-thrombotic iliac vein lesion may cause the distention 36 to form in the left common iliac vein 32 immediately upstream of the non-thrombotic iliac vein lesion. Using the treatment of a stent that is minimally oversized or sized at or about 1:1 with the lumen of the vein, the upstream end 52 of the stent 50 may become positioned within the distention 36, as shown in FIG. 5. The upstream end 52 of the stent 50 may be spaced apart from at least a portion of the wall of the distention 36 and/or the left common iliac vein 32 such that the upstream end 52 of the stent 50 provides little, if any, anchoring force and/or migration resistance. Accordingly, patients having the distention 36 caused by the non-thrombotic iliac vein lesion may result in the stent 50 being even more susceptible to migration due to the lack of anchoring forces provided by the portion of the stent 50 disposed within the distention 36. As a result, one accepted practice is to use a longer stent and/or to use multiple overlapping stents to treat a greater length of the vein to improve migration resistance. However, this may carry other risks because stenting lower into the patient's pelvis area may encounter curves in the venous anatomy, which may subject the stent to bending, the vein to distortion, the patient to pain and/or discomfort from the stent, and/or the stent being subjected to repetitive movement and potential fatigue.

The above discussion leads to an interest in an endoprosthesis having high compression resistance for treating the non-thrombotic iliac vein lesion, low chronic outward force to minimize the Poisson effect, inflammation, and/or pain, and high migration resistance. The endoprostheses and/or methods described herein may offer improvements over existing devices and methods for treating non-thrombotic iliac vein lesions.

Figure 6:
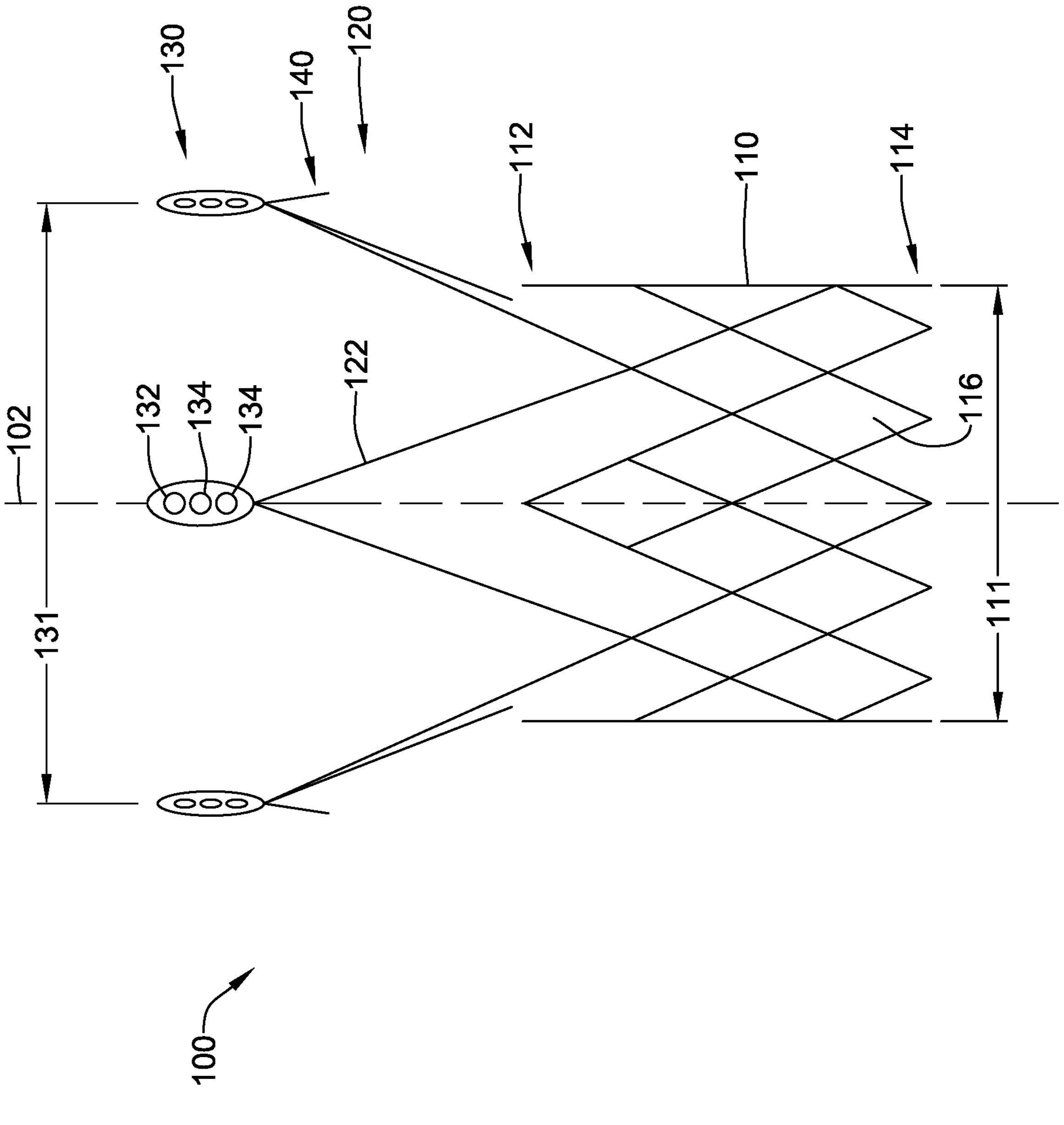
FIG. 6 schematically illustrates selected aspects of an endoprosthesis according to the disclosure.
Figure 7:
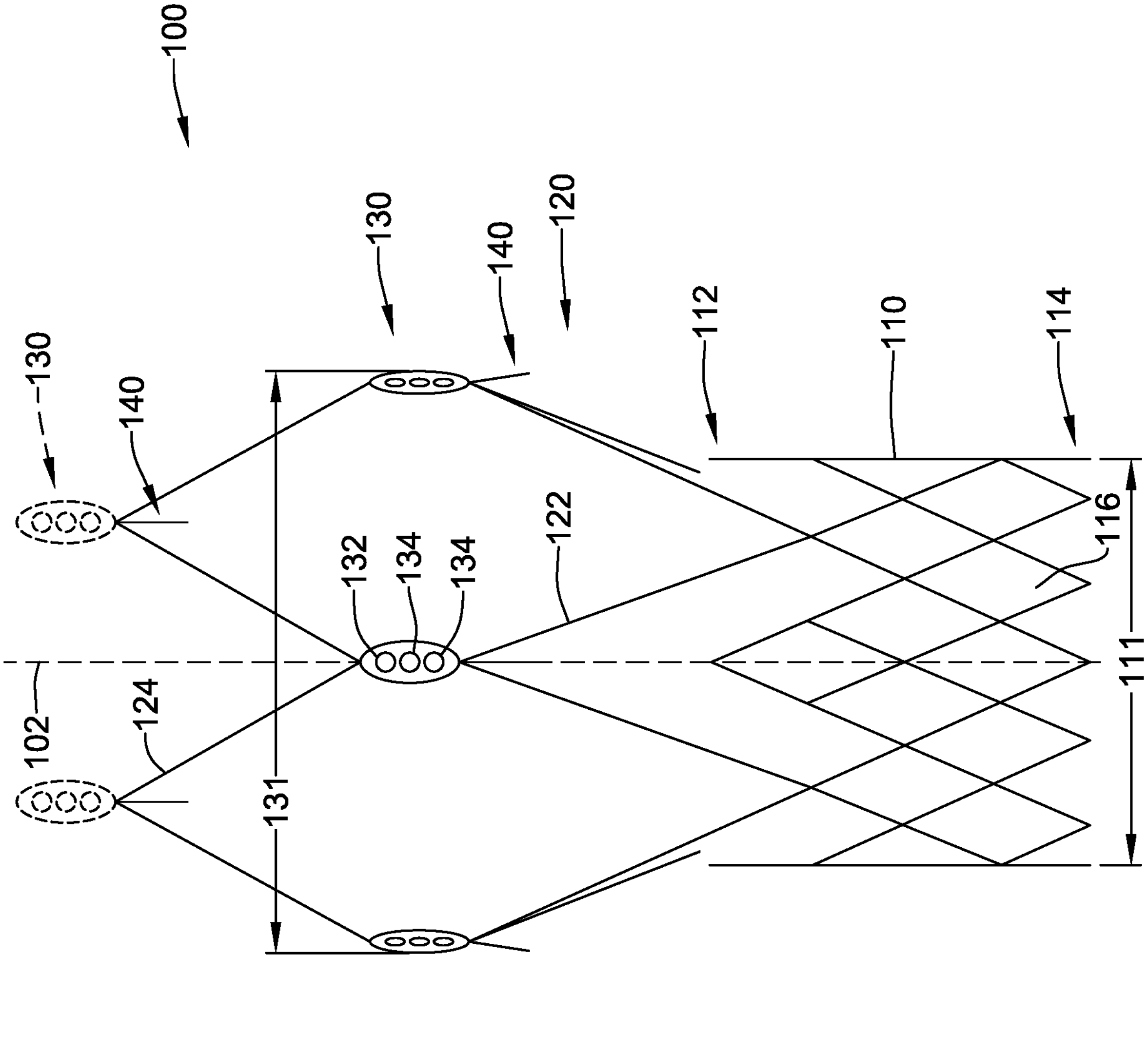
FIG. 7 schematically illustrates selected aspects of an endoprosthesis according to the disclosure.

FIGS. 6-7 schematically illustrate an endoprosthesis 100 for preventing collapse of a vein of a patient at a treatment site, in accordance with the disclosure. The term "stent" may be used interchangeably with the term "endoprosthesis" herein. The endoprosthesis 100 may include an expandable framework 110 defining an outer surface and/or a shape that is generally cylindrical and/or tubular. The endoprosthesis 100 and/or the expandable framework 110 may be defined by and/or may have a central longitudinal axis 102 extending axially and/or longitudinally therethrough. The expandable framework 110 may extend from a first end 112 to a second end 114 opposite the first end 112. In some embodiments, the expandable framework 110 may comprise, include, and/or define a plurality of closed cells 116. The expandable framework 110 may include a lumen extending longitudinally therethrough from the first end 112 to the second end 114. In some embodiments, the first end 112 may be a proximal end and the second end 114 may be a distal end. In some alternative embodiments, the first end 112 may be the distal end and the second end 114 may be the proximal end. The endoprosthesis 100 and/or the expandable framework 110 may be configured to shift between a radially collapsed configuration and a radially expanded configuration. In some embodiments, the endoprosthesis 100 and/or the expandable framework 110 may be self-biased toward the radially expanded configuration. In some embodiments, the endoprosthesis 100 and/or the expandable framework 110 may be self-expandable, mechanically expandable, or balloon expandable. Other configurations are also contemplated.

In some embodiments, the expandable framework 110 may include one or more interwoven filaments forming a braided tubular scaffold in which the one or more interwoven filaments intersect and cross over and/or cross under each other at a plurality of cross-over locations. In some embodiments, the one or more interwoven filaments may include wire(s), thread(s), strand(s), etc. In some embodiments, the one or more interwoven filaments may extend in helical directions while crossing over and under one another along the length of the expandable framework 110. Other configurations are also contemplated.

In some embodiments, the expandable framework 110 may be cut from a tube as a monolithic structure. In some embodiments, the expandable framework 110 may be cut from a flat sheet, rolled to form a tubular structure and/or shape, and then welded together to form the expandable framework 110. Other configurations are also contemplated. Some suitable but non-limiting materials for the endoprosthesis 100, the expandable framework 110, and/or components or elements thereof, for example metallic materials and/or polymeric materials, are described below.

In some embodiments, the expandable framework 110 may have a length measured from the first end 112 to the second end 114 of about 20 millimeters to about 250 millimeters, about 25 millimeters to about 225 millimeters, about 30 millimeters to about 200 millimeters, about 35 millimeters to about 175 millimeters, about 40 millimeters to about 150 millimeters, or another suitable range. In some embodiments, the length of the expandable framework 110 may preferably be between about 20 millimeters and about 80 millimeters.

In some embodiments, the endoprosthesis 100 and/or the expandable framework 110 may have a radial outer dimension or a radial extent of about 4 millimeters to about 30 millimeters, about 5 millimeters to about 25 millimeters, about 6 millimeters to about 20 millimeters, about 8 millimeters to about 18 millimeters, about 10 millimeters to about 16 millimeters, or another suitable range. In some embodiments, the radial outer dimension or the radial extent of the endoprosthesis 100 and/or the expandable framework 110 may be between about 10 millimeters and about 24 millimeters and may more preferably be between about 12 millimeters and about 20 millimeters. Other configurations are also contemplated.

In some embodiments, the endoprosthesis 100 may optionally include a polymeric covering (not shown) extending along and/or secured to the expandable framework 110. In some embodiments, the polymeric covering may cover, occlude, and/or prevent tissue ingrowth through the plurality of closed cells 116. Some suitable but non-limiting materials for the polymeric covering, for example polymeric materials, are discussed below.

In some embodiments, the endoprosthesis 100 may include a plurality of anchoring legs 120 extending axially away from the expandable framework 110. In some embodiments, the plurality of anchoring legs 120 may extend axially away from the first end 112 of the expandable framework 110. In some embodiments, the plurality of anchoring legs 120 may extend proximally from the expandable framework 110. In some embodiments, the plurality of anchoring legs 120 may extend proximally away from the first end 112 of the expandable framework 110. In some alternative embodiments, depending upon the approach used, the plurality of anchoring legs 120 may extend distally from the expandable framework 110. In some embodiments, the plurality of anchoring legs 120 may extend distally away from the first end 112 of the expandable framework 110.

In some embodiments, the plurality of anchoring legs 120 may be configured to shift between a delivery configuration and a deployed configuration. In some embodiments, in the delivery configuration, the plurality of anchoring legs 120 may be configured to extend radially inward of the expandable framework 110. In some embodiments, in the deployed configuration, the plurality of anchoring legs 120 may be configured to extend radially outward of the expandable framework 110 in the radially expanded configuration and/or when the endoprosthesis 100 is unconstrained. In at least some embodiments, the plurality of anchoring legs 120 may be self-biased toward the deployed configuration.

In some embodiments, each anchoring leg of the plurality of anchoring legs 120 may comprise a first segment 122 extending from the expandable framework 110. In some embodiments, each anchoring leg of the plurality of anchoring legs 120 may comprise only the first segment 122 extending from the expandable framework 110, as seen in FIG. 6. It should be noted that for the purpose of illustration only, some instances of the first segment 122 shown in the figures may be incomplete and/or may not be directly attached to the expandable framework 110 because some portions of the endoprosthesis 100 and/or the expandable framework 110 are not shown or are not illustrated completely to improve clarity.

In some embodiments, each anchoring leg of the plurality of anchoring legs 120 may further comprise a second segment 124 extending from the first segment 122 away from expandable framework 110, as shown in FIG. 7. In some embodiments, the first segment 122 and the second segment 124 may be joined together along a middle portion of the plurality of anchoring legs 120.

In some embodiments, the endoprosthesis 100 and/or the plurality of anchoring legs 120 may include a plurality of paddles 130 configured to engage a wall of the vein. In some embodiments, the plurality of paddles 130 may have a generally flattened configuration. In some embodiments, the plurality of paddles 130 may have a circular shape. In some embodiments, the plurality of paddles 130 may preferably have an elongated shape. In some embodiments, the plurality of paddles 130 may have an elongated ovular shape. Other configurations, including combinations thereof, are also contemplated.

In some embodiments, the plurality of paddles 130 may be disposed opposite the first end 112 of the expandable framework 110, and/or at an end of the first segment 122 opposite the first end 112 of the expandable framework 110, as seen in FIG. 6 for example. In some embodiments, the plurality of paddles 130 may be disposed at and/or along the middle portion of the plurality of anchoring legs 120. In some embodiments, at least one paddle of the plurality of paddles 130 may be disposed at and/or along the middle portion of the plurality of anchoring legs 120, as seen in FIG. 7 for example. In some embodiments, each paddle of the plurality of paddles 130 may be disposed at and/or along the middle portion of the plurality of anchoring legs 120. In some embodiments, at least one paddle of the plurality of paddles 130 may be disposed at and/or along the middle portion of the plurality of anchoring legs 120. In some embodiments, each paddle of the plurality of paddles 130 may be disposed at and/or along the middle portion of the plurality of anchoring legs 120. In some embodiments, at least one paddle of the plurality of paddles 130 may be disposed at an end of the second segment 124 disposed opposite the first end 112 of the expandable framework 110 and/or opposite the first segment 122. Other configurations, including combinations thereof, are also contemplated.

In some alternative embodiments, the first segment 122 and the second segment 124 may be coupled together at a joint. In some embodiments, the first segment 122 and the second segment 124 may be coupled together at one paddle of the plurality of paddles 130. In some embodiments, one paddle of the plurality of paddles 130 may form the joint coupling the first segment 122 to the second segment 124. Other configurations, including combinations thereof, are also contemplated.

In some embodiments, at least one paddle of the plurality of paddles 130 may include at least one aperture 132 formed therein. In some embodiments, each paddle of the plurality of paddles 130 may include at least one aperture 132 formed therein. In some embodiments, at least one paddle of the plurality of paddles 130 may include at least one radiopaque marker 134. In some embodiments, at least one paddle of the plurality of paddles 130 may include at least one radiopaque marker 134 fixedly attached thereto. In some embodiments, at least one paddle of the plurality of paddles 130 may include at least one radiopaque marker 134 embedded therein. Other configurations are also contemplated. In some embodiments, each paddle of the plurality of paddles 130 may include at least one radiopaque marker 134. In some embodiments, each paddle of the plurality of paddles 130 may include at least one radiopaque marker 134 fixedly attached thereto. In some embodiments, each paddle of the plurality of paddles 130 may include at least one radiopaque marker 134 embedded therein. Other configurations, including combinations thereof, are also contemplated.

In some embodiments, when the endoprosthesis 100 and/or the plurality of anchoring legs 120 is unconstrained (e.g., when the expandable framework 110 is in the radially expanded configuration and the plurality of anchoring legs is in the deployed configuration), the plurality of paddles 130 defines a radial extent 131 that is at least 10% greater than a radial extent 111 of the expandable framework 110. In some embodiments, when the endoprosthesis 100 and/or the plurality of anchoring legs 120 is unconstrained (e.g., when the expandable framework 110 is in the radially expanded configuration and the plurality of anchoring legs is in the deployed configuration), the plurality of paddles 130 defines a radial extent 131 that is at least 20% greater than a radial extent 111 of the expandable framework 110. In some embodiments, when the endoprosthesis 100 and/or the plurality of anchoring legs 120 is unconstrained (e.g., when the expandable framework 110 is in the radially expanded configuration and the plurality of anchoring legs is in the deployed configuration), the plurality of paddles 130 defines a radial extent 131 that is at least 30% greater than a radial extent 111 of the expandable framework 110. Other configurations are also contemplated.

In at least some embodiments, the expandable framework 110 may be sized and configured to prevent external compression of the vein at the treatment site while simultaneously avoiding radial stretching of the vein (and/or the Poisson effect) at the treatment site. In some embodiments, the radial extent 111 of the expandable framework 110 may be sized within 10% of an inner diameter of the lumen of the vein. In some embodiments, the radial extent 111 of the expandable framework 110 may be sized within 5% of the inner diameter of the lumen of the vein. In some embodiments, the radial extent 111 of the expandable framework 110 may be sized approximately equal to the inner diameter of the lumen of the vein. Other configurations are also contemplated.

In some embodiments, the endoprosthesis 100 may include a plurality of anchoring barbs 140 extending radially outward from the plurality of anchoring legs 120. In some embodiments, the plurality of anchoring barbs 140 may extend radially outward from the plurality of anchoring legs 120 in the deployed configuration. In some embodiments, the plurality of anchoring barbs 140 may be configured to engage the wall of the vein. In some embodiments, the plurality of anchoring barbs 140 may be configured to penetrate into the wall of the vein. Other configurations, including combinations thereto, are also contemplated.

In some embodiments, at least one of the plurality of anchoring barbs 140 may be disposed at the end of the first segment 122 disposed opposite the first end 112 of the expandable framework 110. In some embodiments, each of the plurality of anchoring barbs 140 may be disposed at the end of the first segment 122 disposed opposite the first end 112 of the expandable framework 110. In some embodiments, at least one of the plurality of anchoring barbs 140 may be disposed at the end of the second segment 124 disposed opposite the first segment 122 and/or the first end 112 of the expandable framework 110. In some embodiments, at least one of the plurality of anchoring barbs 140 may be disposed at the joint disposed at and/or along the middle portion of the plurality of anchoring legs 120. In some embodiments, at least one of the plurality of anchoring barbs 140 may be secured to and/or may be fixedly attached to the plurality of paddles 130. In some embodiments, each of the plurality of anchoring barbs 140 may be secured to and/or may be fixedly attached to the plurality of paddles 130. Other configurations, including combinations thereof, are also contemplated.

Figure 8:
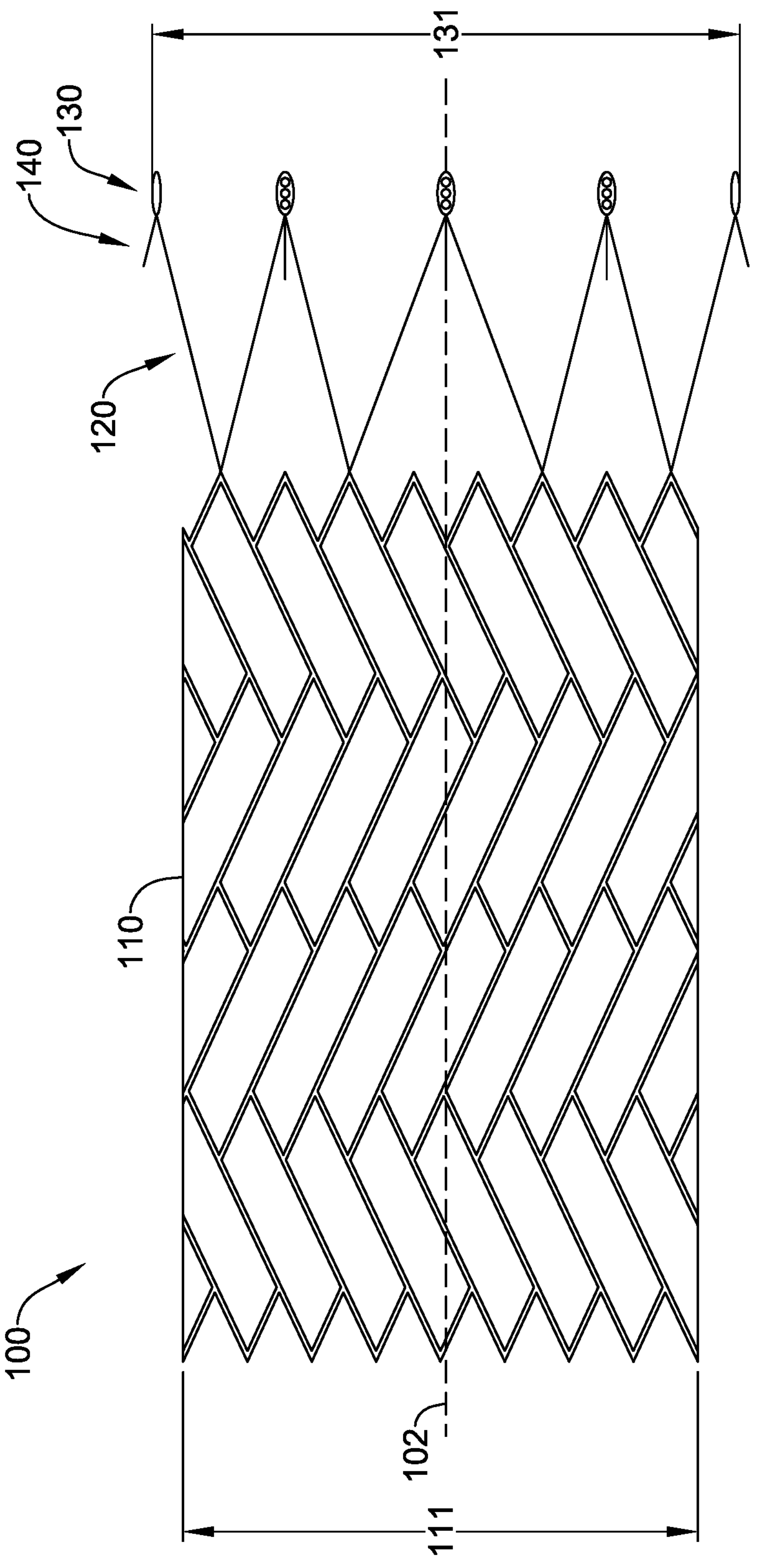
FIGS. 8-9 schematically illustrate selected aspects of alternative endoprostheses according to the disclosure.
Figure 9:
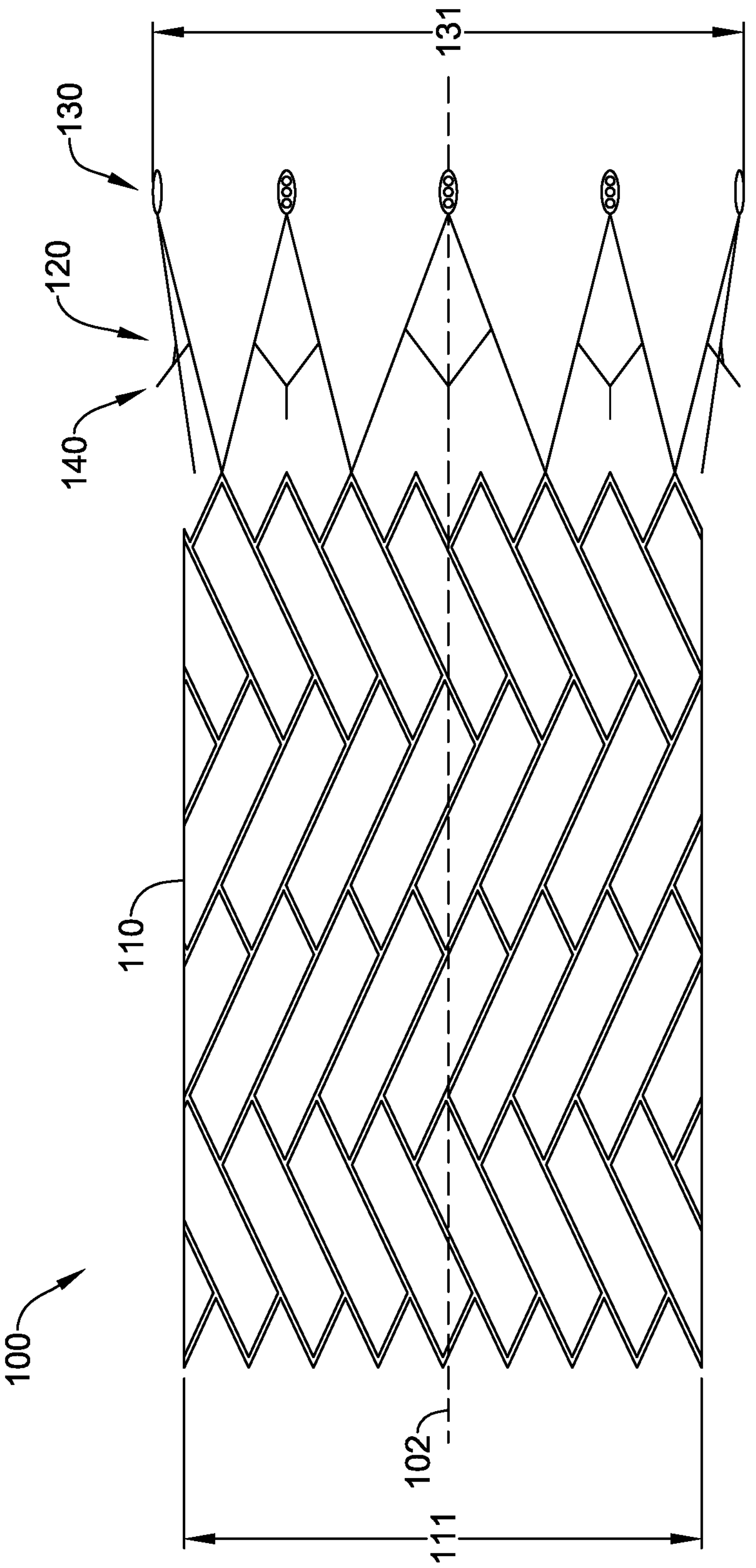

In some embodiments, the plurality of anchoring legs 120 may be integrally formed with the expandable framework 110 as a single monolithic structure and/or from a single monolithic piece of material. In some alternative embodiments, the plurality of anchoring legs 120 may be formed separately from the expandable framework 110 and fixedly attached thereto. FIG. 8 illustrates one alternative example of the endoprosthesis 100 wherein the plurality of anchoring legs 120 has been formed separately from the expandable framework 110 having a plurality of closed cells 116, and later fixedly attached to the first end 112 of the expandable framework 110. In some embodiments, a thickness, a width, and/or a cross-sectional area of the plurality of anchoring legs 120 may be different from the thickness, the width, and/or the cross-sectional area of individual struts or segments of the expandable framework 110. In some embodiments, the thickness, the width, and/or the cross-sectional area of the plurality of anchoring legs 120 may be less than the thickness, the width, and/or the cross-sectional area of individual struts or segments of the expandable framework 110. In some embodiments, the thickness, the width, and/or the cross-sectional area of the plurality of anchoring legs 120 may be greater than the thickness, the width, and/or the cross-sectional area of individual struts or segments of the expandable framework 110. FIG. 9 illustrates another alternative example of the endoprosthesis 100 wherein the plurality of anchoring barbs 140 is positioned differently and/or is spaced apart from the plurality of paddles 130. Other configurations, including combinations thereof, are also contemplated.

In some embodiments, the plurality of paddles 130 may be integrally formed with the plurality of anchoring legs 120 as a single monolithic structure and/or from a single monolithic piece of material. In some embodiments, the plurality of paddles 130 may be formed separately from the plurality of anchoring legs 120 and fixedly attached thereto. Other configurations, including combinations thereof, are also contemplated.

In some embodiments, the plurality of anchoring barbs 140 may be integrally formed with the plurality of anchoring legs 120 and/or the plurality of paddles 130 as a single monolithic structure and/or from a single monolithic piece of material. In some embodiments, the plurality of anchoring barbs 140 may be formed separately from the plurality of anchoring legs 120 and/or the plurality of paddles 130 and fixedly attached thereto. Other configurations, including combinations thereof, are also contemplated.

In some embodiments, the endoprosthesis 100 may be bioabsorbable and/or may include a bioabsorbable material. In some embodiments, the endoprosthesis 100 may include an adhesive material and/or a bioadhesive material. In some embodiments, the adhesive material and/or the bioadhesive material is designed to adhere to biological tissue. For example, the endoprosthesis 100 may be configured to adhere to tissue in situ. Other configurations are also contemplated.

Figure 10:
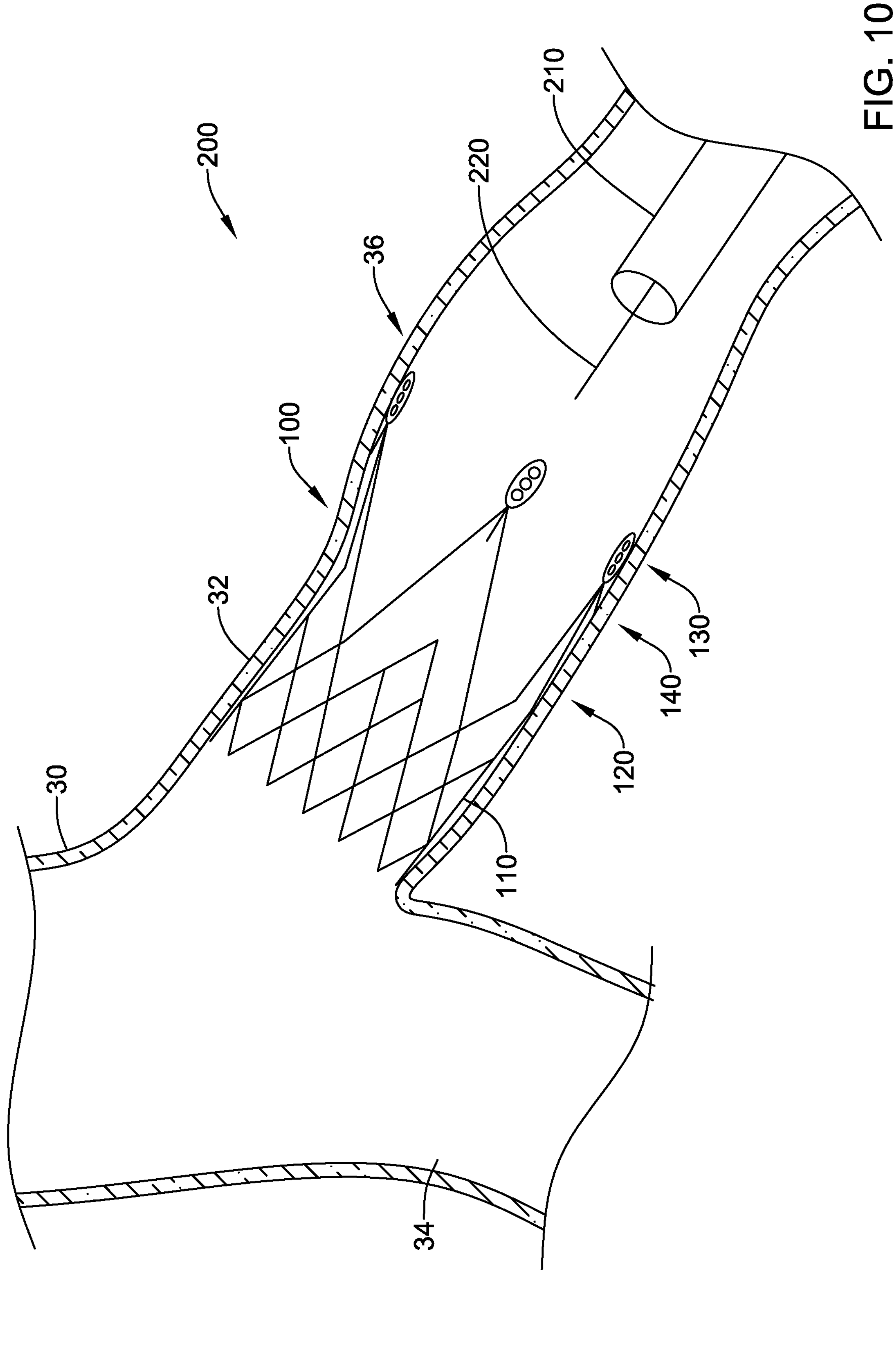
FIG. 10 schematically illustrates selected aspects related to a system and method for preventing collapse of a vein.

FIG. 10 illustrates selected aspects of a system 200 and method for preventing collapse of a vein (e.g., the left common iliac vein 32). The system 200 may include a delivery catheter 210 having a lumen extending therethrough. The system 200 may include the endoprosthesis 100, wherein the endoprosthesis 100 is disposable within a distal portion of the lumen of the delivery catheter 210 in the radially collapsed configuration.

The method may include positioning a distal end of the delivery catheter 210 adjacent a treatment site (e.g., the non-thrombotic iliac vein lesion) within the vein (e.g., the left common iliac vein 32). The method may include deploying the endoprosthesis 100 at the treatment site, as seen in FIG. 10. In at least some embodiments, after deploying the endoprosthesis 100 at the treatment site, the plurality of anchoring legs 120 extends upstream from the expandable framework 110 within the vein (e.g., the left common iliac vein 32).

In some embodiments, prior to positioning the distal end of the delivery catheter 210 adjacent the treatment site, the delivery catheter 210 may be advanced into the vein at a location upstream of the treatment site. For example, in some procedures, the access site (e.g., the location upstream of the treatment site) may be the popliteal vein, the posterior tibial vein, or another suitable upstream access location, depending on the location of the treatment site. In some alternative embodiments, prior to positioning the distal end of the delivery catheter 210 adjacent the treatment site, the delivery catheter 210 may be advanced into the vein at a location downstream of the treatment site. For example, in some procedures, the access site (e.g., the location downstream of the treatment site) may be the jugular vein. In at least some embodiments, the treatment site may be a non-thrombotic iliac vein lesion.

Figure 11:
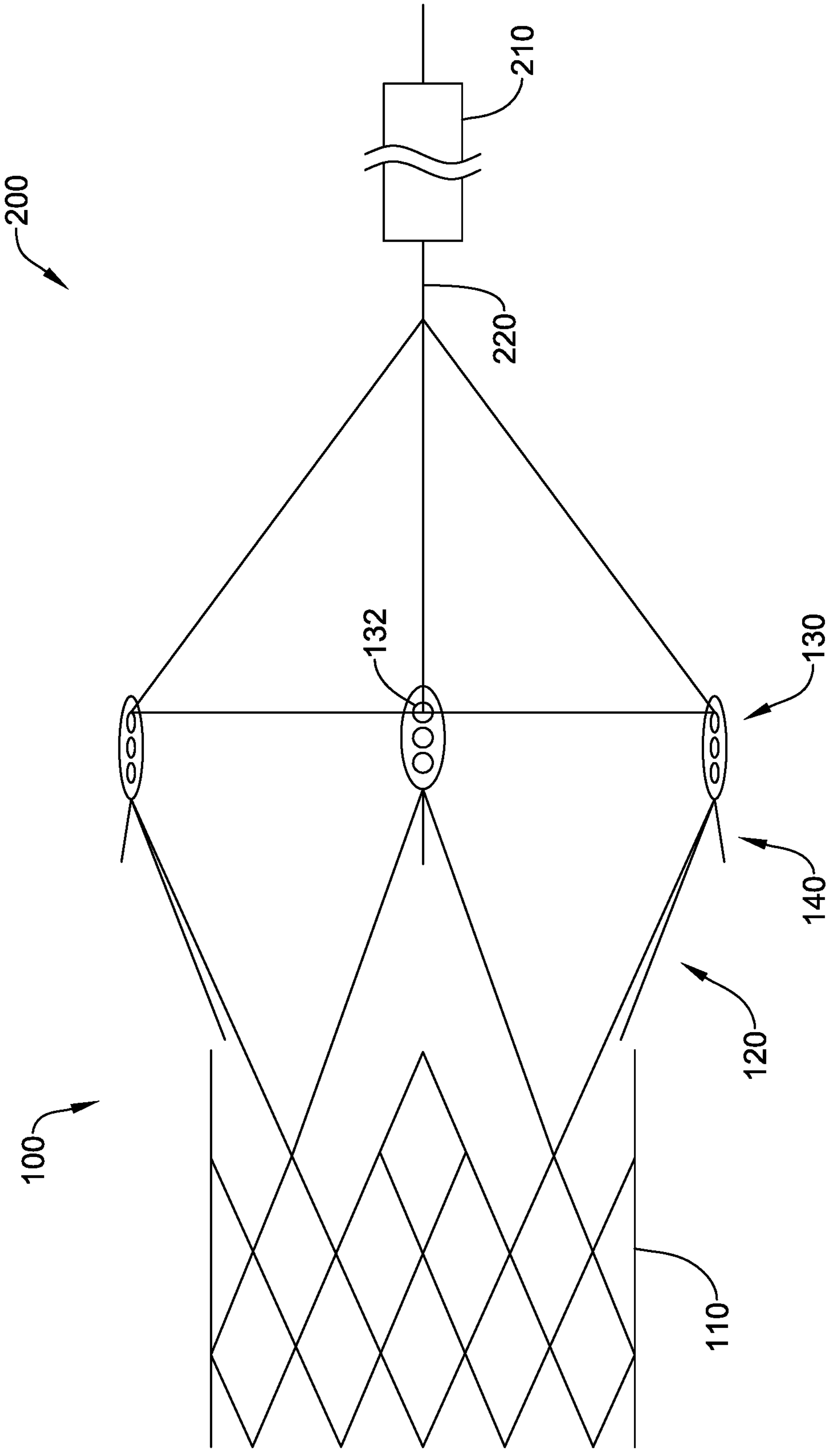
FIG. 11 schematically illustrates selected aspects related to a system and method for preventing collapse of a vein.

In some embodiments, the system may include at least one filament 220 couplable to the plurality of anchoring legs 120 of the endoprosthesis 100 and may extend within the lumen of the delivery catheter 210. In at least some embodiments, the at least one filament 220 may be coupled to the plurality of anchoring legs 120 of the endoprosthesis 100 and may extend within the lumen of the delivery catheter 210 (e.g., FIGS. 11-12). In some embodiments, the at least one filament 220 may be releasably coupled to the plurality of paddles 130 of the endoprosthesis 100, as seen in FIG. 11. In some embodiments, the at least one filament 220 may be engaged with and/or may pass through the at least one aperture 132 formed in the plurality of paddles 130 of the endoprosthesis 100.

In some embodiments, after deploying the endoprosthesis 100 at the treatment site, the at least one filament 220 may be decoupled from and/or disconnected from the endoprosthesis 100, the plurality of anchoring legs 120, and/or the plurality of paddles 130, as shown in FIG. 10. After decoupling the at least one filament 220 from the endoprosthesis 100, the plurality of anchoring legs 120, and/or the plurality of paddles 130, the delivery catheter 210 and the at least one filament 220 may be removed from the treatment site, the vein, and/or the patient.

In some embodiments, the method may include recapturing the endoprosthesis 100 within the lumen of the delivery catheter 210 and repositioning the endoprosthesis 100 at and/or adjacent to the treatment site. In some embodiments, the at least one filament 220 may be configured to shift the plurality of anchoring legs 120 from the deployed configuration toward and/or to the delivery configuration at the treatment site to facilitate recapture of the endoprosthesis 100. For example, the at least one filament 220 may be configured to guide and/or pull the plurality of anchoring legs 120, the expandable framework 110, and/or the endoprosthesis 100 into the lumen of the delivery catheter 210 when recapturing the endoprosthesis 100.

In some embodiments, the method may include recapturing the endoprosthesis 100 within the lumen of the delivery catheter 210 and removing the endoprosthesis 100 from the treatment site and/or the patient. For example, if deployment failure occurs and/or an incorrect size of the endoprosthesis 100 is selected, the endoprosthesis 100 may need to be removed from the treatment site and/or the patient and replaced with a new one. In at least some embodiments, the method may include, after removing the endoprosthesis 100 from the treatment site and/or the patient, repeating the positioning step and the deploying step of the method to replace the endoprosthesis 100 at the treatment site.

Figure 12:
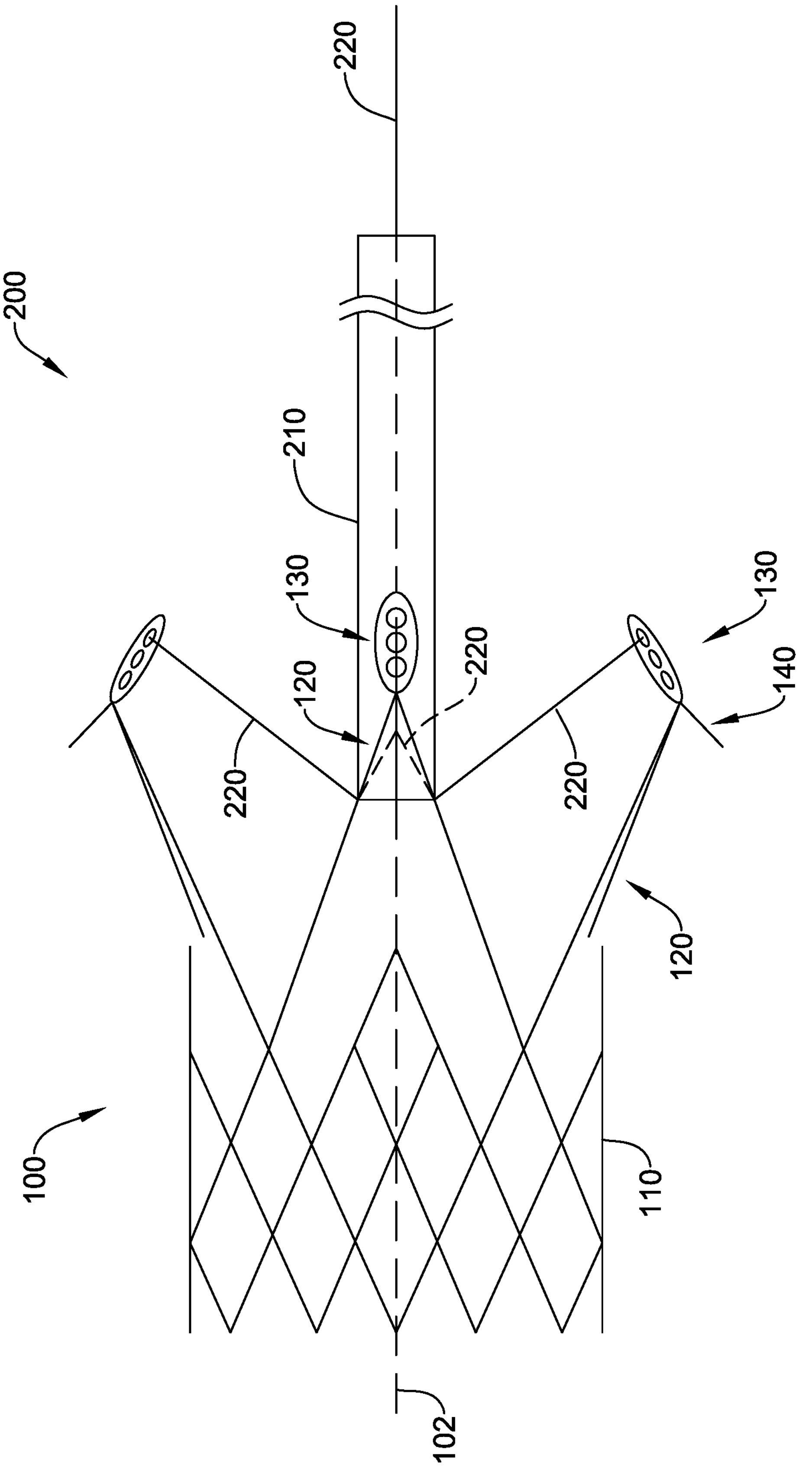
FIG. 12 schematically illustrates selected aspects related to a system and method for preventing collapse of a vein.

In some embodiments, the at least one filament 220 and the delivery catheter 210 may be configured to cooperate with each other to change an angle of the plurality of anchoring barbs 140 relative to the central longitudinal axis 102 of the endoprosthesis 100 and/or the expandable framework 110, as shown in FIG. 12. In some embodiments, the delivery catheter 210 may be advanced distally along the at least one filament 220 relative to the endoprosthesis 100 and/or the plurality of paddles 130 such that the plurality of anchoring legs 120 and/or the plurality of paddles 130 is pulled radially inward toward the central longitudinal axis 102. In doing so, free ends of the plurality of anchoring barbs 140 may be tilted outward relative to the central longitudinal axis 102. In one example, where the plurality of anchoring barbs 140 are coupled to a distal end of the plurality of paddles 130, the at least one filament 220 and the delivery catheter 210 may cooperate with each other to pull a proximal end of the plurality of paddles 130 radially inward relative to the distal end of the plurality of paddles 130 such that the plurality of paddles 130 is tilted and/or angled relative to the central longitudinal axis 102, thereby causing the free end(s) of the plurality of anchoring barbs 140 to angle further outward relative to the central longitudinal axis 102.

In some embodiments, the system may include an elongate inner member disposed within the lumen of the delivery catheter 210. In some embodiments, the elongate inner member may be a tubular member having a lumen extending therein and/or therethrough. In some embodiments, the lumen of the elongate inner member may be a guidewire lumen. In some embodiments, the lumen of the elongate inner member may be used for irrigation and/or aspiration. Other configurations are also contemplated. In some alternative embodiments, the elongate inner member may be a solid shaft.

In some embodiments, the elongate inner member may be axially translatable relative to the delivery catheter 210. In some embodiments, the delivery catheter 210 may be translatable in a proximal direction relative to the elongate inner member. For example, the elongate inner member may be held in a fixed position while the delivery catheter 210 is withdrawn proximally. In some embodiments, the delivery catheter 210 and the elongate inner member may be configured to be advanced to the treatment site together and/or simultaneously. In at least some embodiments, during advancement to the treatment site, the delivery catheter 210 and the elongate inner member may be disposed and/or held in an axially fixed relationship relative to each other. Other configurations are also contemplated.

In some embodiments, the endoprosthesis 100 and/or the expandable framework 110 may be disposed within the lumen of the delivery catheter 210 in the radially collapsed configuration. In some embodiments, the delivery catheter 210 may constrain the endoprosthesis 100 and/or the expandable framework 110 in the radially collapsed configuration when the endoprosthesis 100 is disposed within the lumen of the delivery catheter 210. In some embodiments, the endoprosthesis 100 may be disposed radially between the delivery catheter 210 and the elongate inner member. In some embodiments, the endoprosthesis 100 may be attached to, crimped onto, and/or otherwise retained by the elongate inner member. Other configurations are also contemplated.

Figure 13:
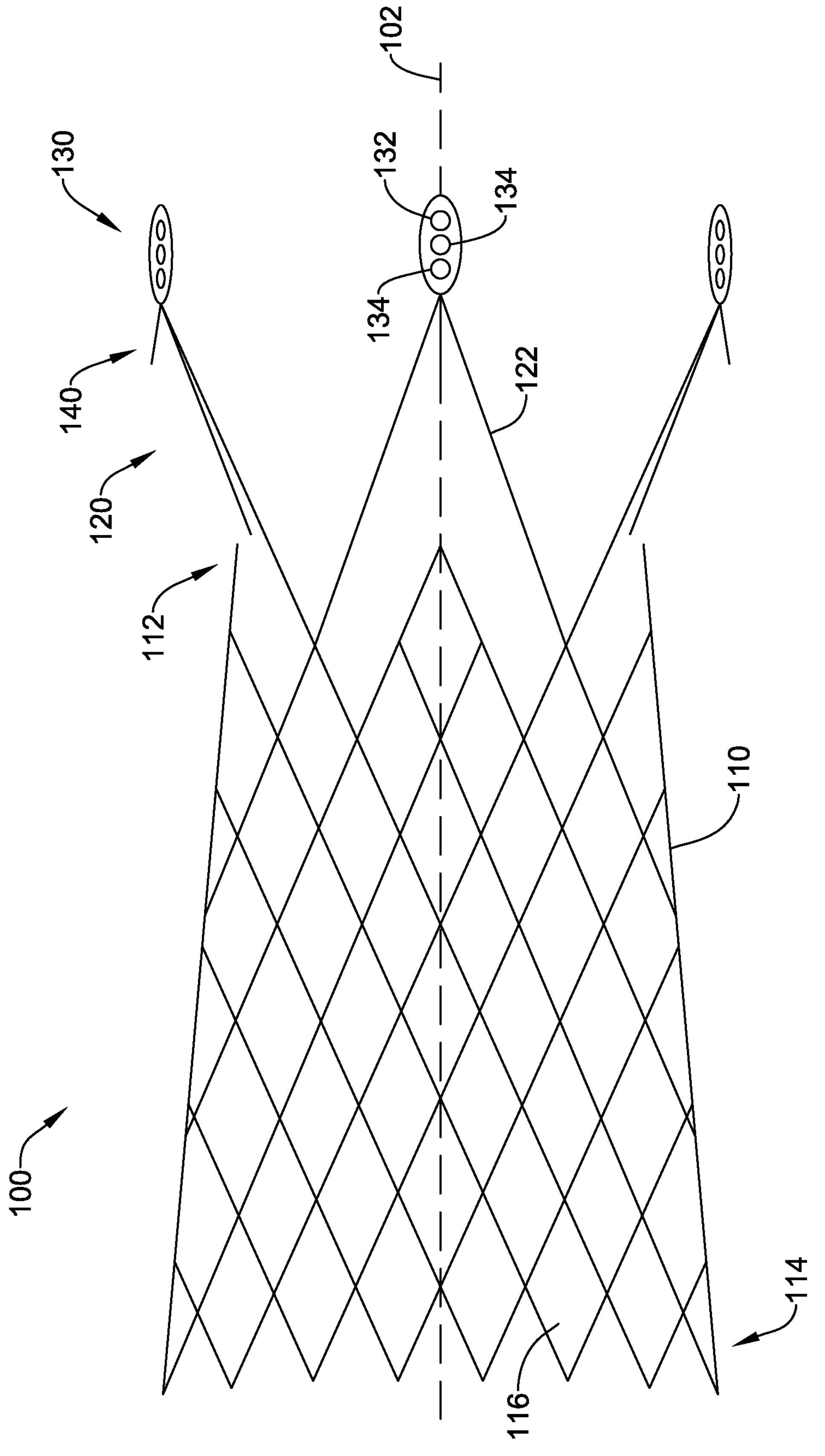
FIG. 13 schematically illustrates selected aspects of an endoprosthesis according to the disclosure.

FIG. 13 illustrates an alternative configuration of the endoprosthesis 100. The endoprosthesis 100 of FIG. 13 may be similar to and/or the same as the endoprostheses 100 of FIG. 6, except as described herein.

In some embodiments, the endoprosthesis 100 may include an expandable framework 110 defining an outer surface and/or a shape that is tapered and/or generally conical. In some embodiments, the expandable framework 110 may be tapered radially outward from the first end 112 toward the second end 114. In some embodiments, the first end 112 may have a first radial extent and the second end 114 may have a second radial extent, wherein the second radial extent is greater than the first radial extent. In some embodiments, the lumen extending longitudinally through the expandable framework 110 from the first end 112 to the second end 114 may be tapered radially outward from the first end 112 toward the second end 114.

In some embodiments, the expandable framework 110 may be tapered constantly from the first end 112 to the second end 114. In some embodiments, the expandable framework 110 may be tapered intermittently along the length of the expandable framework 110. For example, the expandable framework 110 may be tapered in steps or segments with intervening steps or segments having a generally constant radial extent. Other configurations are also contemplated.

Similar to other embodiments described herein, a radial extent of the plurality of paddles 130 may be greater than the first radial extent of the first end 112. Relative sizing of the second radial extent and/or the second end 114 compared to the radial extent of the plurality of paddles 130 may depend on the length of the expandable framework 110. In some embodiments wherein the expandable framework 110 has a longer or extended length, the second radial extent may be approximately equal to the radial extent of the plurality of paddles 130, or the second radial extent may be greater than the radial extent of the plurality of paddles 130. In some embodiments, the second radial extent may be less than the radial extent of the plurality of paddles 130, similar to the endoprostheses shown in FIGS. 6-9 and 11-12.

The endoprosthesis 100 of FIG. 13 may be useful for in venous applications where the vein changes diameter and/or size along its length and/or at or along the treatment site. The second radial extent may be chosen and/or may be sufficient to accommodate the change in diameter of the vein over a given length of the vein. Other applications and/or uses are also contemplated.

The materials that can be used for the various components of the system and the various elements thereof disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the endoprosthesis, the expandable framework, the plurality of anchoring legs, the plurality of paddles, the plurality of anchoring barbs, the delivery catheter, the at least one filament, the polymeric covering, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MM) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MM image. The system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A method of preventing collapse of a vein, comprising:

positioning a distal end of a delivery catheter adjacent a treatment site within the vein, the delivery catheter having a lumen extending therethrough; and deploying an endoprosthesis at the treatment site, the endoprosthesis including:

an expandable framework configured to shift between the radially collapsed configuration and a radially expanded configuration, the expandable framework having a first end and a second end opposite the first end; and a plurality of anchoring legs extending axially away from the first end of the expandable framework, the plurality of anchoring legs being configured to shift between a delivery configuration and a deployed configuration;

wherein, in the deployed configuration, the plurality of anchoring legs is configured to extend radially outward of the expandable framework in the radially expanded configuration;

wherein after deploying the endoprosthesis at the treatment site, the plurality of anchoring legs extends upstream from the expandable framework within the vein;

wherein the treatment site is a non-thrombotic iliac vein lesion.

2. The method of claim 1, wherein prior to positioning the distal end of the delivery catheter adjacent the treatment site, the delivery catheter is advanced into the vein at a location upstream of the treatment site.

3. The method of claim 1, further comprising:

recapturing the endoprosthesis within the lumen of the delivery catheter and repositioning the endoprosthesis at and/or adjacent to the treatment site.

4. The method of claim 1, wherein the expandable framework comprises a plurality of closed cells.

* * * * *